(12) United States Patent
Zou et al.

(10) Patent No.: US 8,457,435 B2
(45) Date of Patent: Jun. 4, 2013

(54) METHODS AND SYSTEMS FOR EXTENDED ULTRASOUND IMAGING

(75) Inventors: Yaoxian Zou, Shenzhen (CN); Yong Tian, Shenzhen (CN); Bin Yao, Shenzhen (CN); Qinjun Hu, Shenzhen (CN)

(73) Assignee: Shenzhen Mindray Bio-Medical Electronics Co., Ltd, Shenzhen (CN)

( * ) Notice: Subject to any disclaimer, the term of this patent is extended or adjusted under 35 U.S.C. 154(b) by 261 days.

(21) Appl. No.: 13/156,087

(22) Filed: Jun. 8, 2011

(65) Prior Publication Data

US 2011/0299755 A1 Dec. 8, 2011

(30) Foreign Application Priority Data

Jun. 8, 2010 (CN) .......................... 2010 1 0201592

(51) Int. Cl.
*G06K 9/36* (2006.01)
(52) U.S. Cl.
USPC ........... 382/264; 382/219; 382/284; 382/294; 358/540; 358/450

(58) Field of Classification Search
USPC .......... 382/219, 278, 282, 284, 294; 358/537, 358/540, 450, 453
See application file for complete search history.

(56) References Cited

U.S. PATENT DOCUMENTS

| | | | |
|---|---|---|---|
| 6,554,770 B1 | 4/2003 | Sumanaweera et al. | |
| 6,605,042 B2 | 8/2003 | Dong et al. | |
| 7,308,139 B2 * | 12/2007 | Wentland et al. | 382/181 |
| 7,738,121 B2 * | 6/2010 | Spalding | 356/638 |
| 7,774,052 B2 * | 8/2010 | Burton et al. | 600/544 |
| 7,864,999 B2 * | 1/2011 | Chang et al. | 382/128 |
| 7,881,878 B2 * | 2/2011 | Burrus et al. | 702/28 |
| 2007/0255137 A1 | 11/2007 | Sui et al. | |

FOREIGN PATENT DOCUMENTS

| | | |
|---|---|---|
| CN | 1748650 A | 3/2006 |
| CN | 1839760 A | 10/2006 |
| CN | 101455576 A | 6/2009 |

* cited by examiner

*Primary Examiner* — Yosef Kassa
(74) *Attorney, Agent, or Firm* — Kory D. Christensen; Stoel Rives LLP (57) ABSTRACT

An ultrasound imaging system and method provides for extended imaging.

24 Claims, 6 Drawing Sheets

METHODS AND SYSTEMS FOR EXTENDED ULTRASOUND IMAGING

CROSS-REFERENCE TO RELATED APPLICATIONS

This application claims the benefit of Chinese Patent Application No. 201010201592.5, filed on Jun. 8, 2010, which is incorporated herein by reference.

TECHNICAL FIELD

The following disclosure relates to ultrasound imaging.

SUMMARY OF THE INVENTION

An ultrasound imaging system, according to one embodiment, determines a floating image and a registering image, divides sub-areas from the floating image, determines one or more reference points in each sub-area, determines searching areas in the registering image for the reference points, searches for points matching the reference points in the searching areas corresponding to the reference points, calculates motion vectors of the reference points relative to the registering image according to the matching points, fits the motion vectors to obtain converting parameters between the floating image and the registering image, and splices the floating image and the registering image to obtain an extended image.

DETAILED DESCRIPTION

Ultrasound devices are typically used to observe internal tissues and structures of the human body. However, the visual field of the ultrasound image is limited by the width of the probe. For large tissues or structures, only portions of them can be displayed on the screen. The doctor has to move the probe back and forth and reconstruct the whole tissues or structures from memory. When measuring the tissues or structures, the doctor must adjust the probe to place the area to be measured within a single image. If the area exceeds the visual field of the image, the measurement cannot be performed.

Extended imaging is designed to solve these problems. An extended imaging system obtains a series of 2D slice images by moving the probe in the same plane and splices the slice images based on a correlation between the slice images to form an extended image containing all the content of the series of slice images. From the extended image, the doctor may obtain information about the examined tissues or structures quickly, improving the speed of examination.

Extended imaging includes a registering step and a splicing step. The registering step is used to register the adjacent frames (slice images) to calculate converting parameters based on the correlation between the adjacent frames. The splicing step is used to splice the adjacent frames according to the converting parameters calculated in the registering step.

Existing methods for registering the adjacent frames have a number of disadvantages. For example, the number of calculations required to create extended images is huge, which slows down the speed of imaging. Also, fault-tolerance is typically poor because of noise, motion of tissues or structures, or operations of the user, etc.

Figure 1:
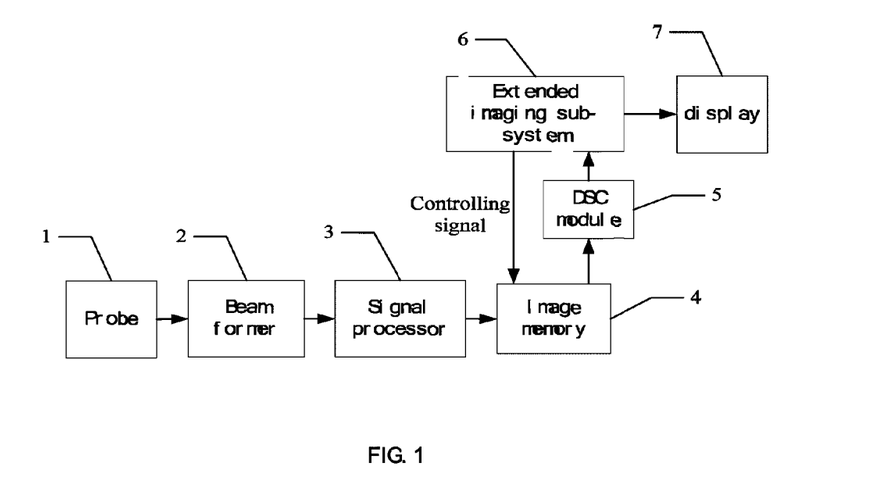
FIG. 1 is a block diagram of an embodiment of an ultrasound imaging system.

FIG. 1 shows an ultrasound imaging system according to one embodiment. The system may include a probe 1, a beam former 2, a signal processor 3, an image memory 4, a DSC (Digital Scan Conversion) module 5, an extended imaging sub-system 6, and a display 7.

The probe 1 slides continually on the surface of the body to be scanned, transmitting ultrasound waves into the body and receiving echoes reflected by tissues of the body. The received echoes are converted into electrical signals, which are sent to the beam former 2. The beam former 2 is used to focus on echoes coming from a particular area and/or depth. The signals outputted from the beam former 2 are processed by the signal processor 3 to obtain images. The images are then stored in the image memory 4. In one embodiment, the extended imaging sub-system 6 sends controlling signals to the image memory 4. The image memory 4 transmits the stored images to the DSC module 5, which performs digital scan conversion and sends the converted images to the extended imaging sub-system 6. The extended imaging sub-system 6 then performs extended imaging and sends the extended images to the display 7 to be viewed by a user.

In one embodiment, the ultrasound imaging system described above is a real-time system. In other words, the extended imaging is performed in parallel with obtaining ultrasound images. During extended imaging, the probe 1 continues to scan the body and the images obtained are continuously stored in the image memory 4. The images stored in the image memory 4 are read out and spliced one by one to obtain extended images. Defining the images read out from the image memory 4 as $I_1, I_2, \ldots, I_i, \ldots$, for a real-time system, $I_i$ is the latest image that is stored into the image memory 4 when image $I_{i-1}$ is spliced. After the image $I_{i-1}$ is spliced, image I will be spliced. After the image I is spliced, image $I_{i+1}$ will be spliced, and so on, until the extended imaging process is instructed to end.

In another embodiment, the ultrasound imaging system may also be non-real-time system. That is, the extended imaging and the obtaining ultrasound images are not performed at the same time. The extended imaging process will be performed after the process of obtaining the ultrasound images process is completed. Defining the images read out from the image memory 4 as $I_1, I_2, \ldots, I_i, \ldots$, for a non-real-time system, $I_i = I_{i-1+\Delta}$. $\Delta$ is the image interval between two splicings, which may be set according to actual conditions.

Because the probe 1 continually slides on the surface of the body, the overlapping portions of adjacent images are typically large. As a result, there may be interval between the images that are read out for splicing. The value of the interval may be set according to actual conditions. For example, the interval may be 1 frame or 3 frames. The value of the interval may also be adjusted automatically according to offset value of preceding images. Usually, the value of the interval is inversely proportional to the offset value.

Figure 2:
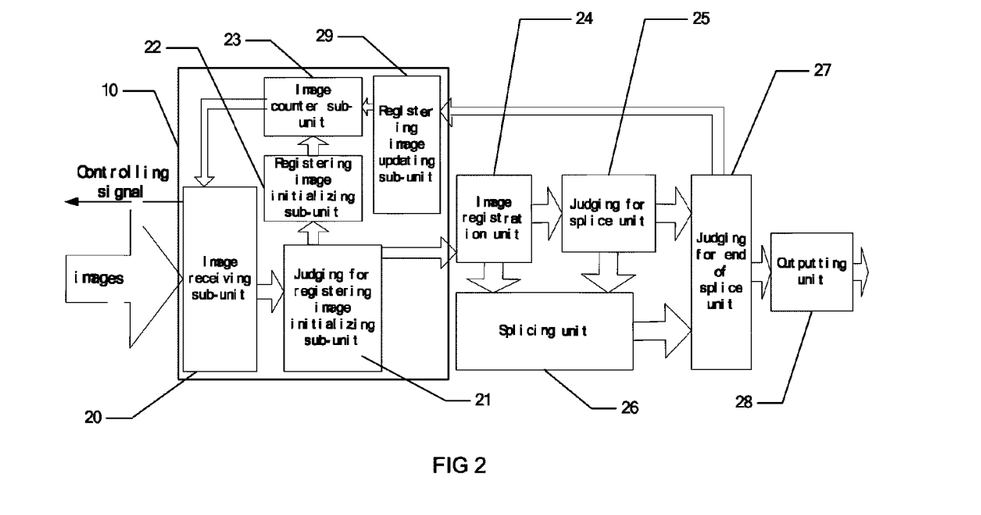
FIG. 2 is a block diagram of an embodiment of an extended imaging system.

FIG. 2 illustrates an embodiment of an extended imaging sub-system 6. The extended imaging sub-system 6 may include a floating/registering image determining unit 10, an image registration unit 24, a judging for splice unit 25, a splicing unit 26, a judging for end of splice unit 27, and an outputting unit 28. The floating/registering image determining unit 10 may include an images receiving sub-unit 20, a judging for registering image initializing sub-unit 21, a registering image initializing sub-unit 22, an image counter sub-unit 23, and a registering image updating sub-unit 29.

In one embodiment, the images receiving sub-unit 20 sends controlling signals to the images memory 4 to cause the images memory 4 to send the latest image that is stored into the images memory 4 to the DSC module 5 to be converted, and then receive the image converted by the DSC module 5. Thereafter, the judging for registering image initializing sub-unit 21 judges whether the registering image need to be initialized. If the image received is not the first image read out from the image memory 4 to be registered during current extended imaging process, the judging for registering image initializing sub-unit 21 judges that the registering image need not be initialized, and the received image is designated as a floating image and is transmitted to the image registration unit 24 for registering. If, however, the image received is the first image read out from the image memory 4 to be registered during current extended imaging process, the judging for registering image initializing sub-unit 21 judges that the registering image need to be initialized, and the received image is transmitted to the registering image initializing sub-unit 22. The registering image initializing sub-unit 22 initializes this image as the registering image. At the same time, the registering image initializing sub-unit 22 sends a image counting instruction to the image counter sub-unit 23 to make it add 1 to the count of images. Then, the image counter sub-unit 23 gives an instruction for reading the next image to the images receiving sub-unit 20. The images receiving sub-unit 20 receives the instruction and then sends controlling signals to the images memory 4 to read out next image.

After the image is registered by the image registration unit 24, different processes may occur. A first process may include transmitting the registered image to the judging for splice unit 25, after which the judging for splice unit 25 judges whether this image need to be spliced (the judging process will be described below). If it needs to be spliced, the image frame is transmitted to the splicing unit 26 for being spliced. If the image does not need to be spliced, the judging for end of splice unit 27 judges whether it is the end of the splicing.

A second process may include directly transmitting the registered image to the splicing unit 26 for being spliced. After the image frame is spliced, the judging for end of splice unit 27 judges whether it is end of the splicing.

In one embodiment, the conditions for the judging for end of splice unit 27 to judge that it is the end of splicing may be different for real-time system and for non-real-time system. For a real-time system, when receiving an instruction for ending extended imaging, the judging for end of splice unit 27 judges that it is the end of splicing. For a non-real-time system, the judging for end of splice unit 27 judges that it is the end of splicing after all images stored in the image memory 4 are processed.

When the judging for end of splice unit 27 judges that it is not the end of splicing, the registering image updating sub-unit 29 updates the registering image and sends a image counting instruction to the image counter sub-unit 23 to make it add 1 to the count of images. Then, the image counter sub-unit 23 gives an instruction for reading the next image frame to the images receiving sub-unit 20. The images receiving sub-unit 20 receives the instruction and then sends controlling signals to the images memory 4 to read out the next image.

In one embodiment, when the judging for end of splice unit 27 judges that it is the end of splicing, the outputting unit 28 outputs the spliced extended images for display.

Figure 3:
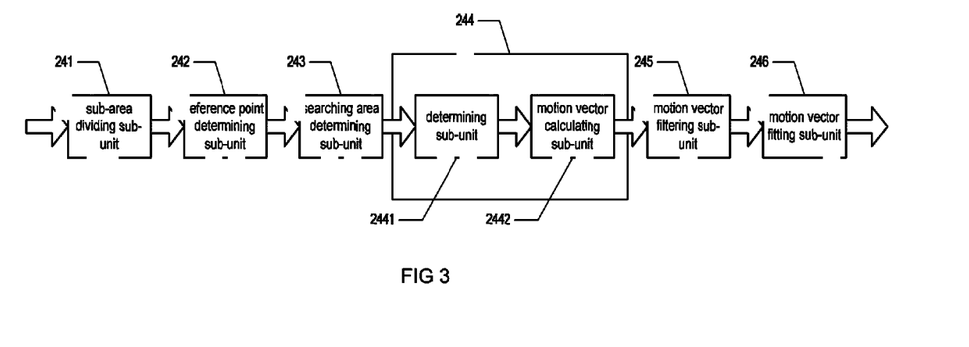
FIG. 3 is a block diagram of an embodiment of an apparatus for registering images.

FIG. 3 shows further details of the image registration unit 24 of FIG. 2. The image registration unit 24 may include a sub-area dividing sub-unit 241, a reference point determining sub-unit 242, a searching area determining sub-unit 243, a motion vector processing sub-unit 244, a motion vector filtering sub-unit 245 and a motion vector fitting sub-unit 246.

In one embodiment, the sub-area dividing sub-unit 241 divides some sub-areas from the floating image. The reference point determining sub-unit 242 determines one or more reference points in each sub-area. The searching area determining sub-unit 243 determines a searching area for each of the reference points in the registering image. Accordingly, for each reference point, there is a corresponding searching area in the registering image individually. In this disclosure, the searching area corresponding to a reference point is referred to as the "searching area of the reference point".

The motion vector processing sub-unit 244 searches matching points that match with the reference points in the searching areas of these reference points. Then, the motion vector processing sub-unit 244 calculates a motion vector of each reference point relating to the registering image using the reference point and its corresponding matching points. Hereinafter, the motion vector is referred to as the "motion vector of the reference point." The motion vector filtering sub-unit 245 is configured to eliminate wrong motion vectors. The motion vector fitting sub-unit 246 is configured to fit the motion vectors to obtain the relationship between the floating images and the registering image.

The motion vector processing sub-unit 244 may include a determining sub-unit 2441 and a motion vector calculating sub-unit 2442. The determining sub-unit 2441 is configured to determine a starting point of a "climbing method" in the registering image (which will be described in detail below). The motion vector calculating sub-unit 2442 determines a neighborhood around the starting point, calculates target function value F (described below) for each point in the neighborhood, and judges whether the point whose value is the optimum value among the values calculated is the starting point. If it is, the starting point is the matching point. The motion vector calculating sub-unit 2442 calculates the motion vector using the matching point and the reference point. If it is not, the point whose value is the optimum value is designated as the starting point and the steps above are repeated until the motion vector is calculated, as described more fully below.

Figure 4:
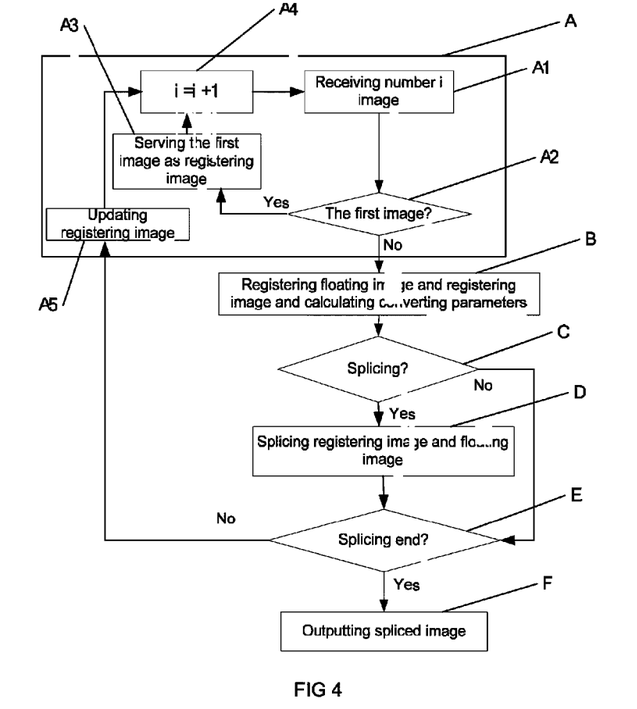
FIG. 4 is a flow diagram of an embodiment of method for extended imaging.

FIG. 4 illustrates an exemplary work flow of the extended imaging sub-system 6, which may include:

Step A: determining the floating image and registering image.

The extended imaging sub-system 6 sends controlling signals to the image memory 4 to instruct the image memory 4 to transmit the ith image to the DSC module for digital scan converting. Then, the converted image is transmitted to the extended imaging sub-system 6 for extended imaging. Hereinafter, the image for extended imaging is called the "floating image."

Step A may include the following sub-steps:

Step A1: receiving the ith image that is converted by the DSC module 5;

Step A2: judging whether the ith image is the first image received to be registered during current extended imaging process. If it is, then step A3 is performed. If not, the ith image is designated as a floating image, and step B is performed;

Step A3: the first image is designated as the registering image;

Step A4: incrementing i (i.e., i=i+1), then performing step A1; and

Step A5: updating the registering image, then performing step A4.

The registering image is used to register with the floating image and calculate the converting parameters between the registering image and the floating image. The image that is updated as the registering image for the next registering in step A5 may be the current floating image or the image that is obtained by splicing the current floating image and the current registering image.

Step B: registering the floating image and the registering image and calculating the converting parameters between the registering image and the floating image.

Step C: judging whether it is needed to perform the splicing process. If it is, then step D is performed; if not, step E is performed.

Whether to perform the splicing process may be determined according to the value of the converting parameters, which will be described in detail below.

Step D: splicing the floating image and the registering image using the converting parameters.

Step E: judging whether it is the end of the splicing process. If so, step F is performed; If not, step A5 is performed.

For real-time systems, the end of the splicing process is determined according to input of users. For non-real-time systems, the splicing process ends when i>N, where N is the whole number of the images stored in the image memory 4.

Step F: outputting the spliced image.

Among these steps, step C may not be needed in all embodiments. The floating image and the registering image may be directly spliced after their being registered without the judging step C.

Figure 5:
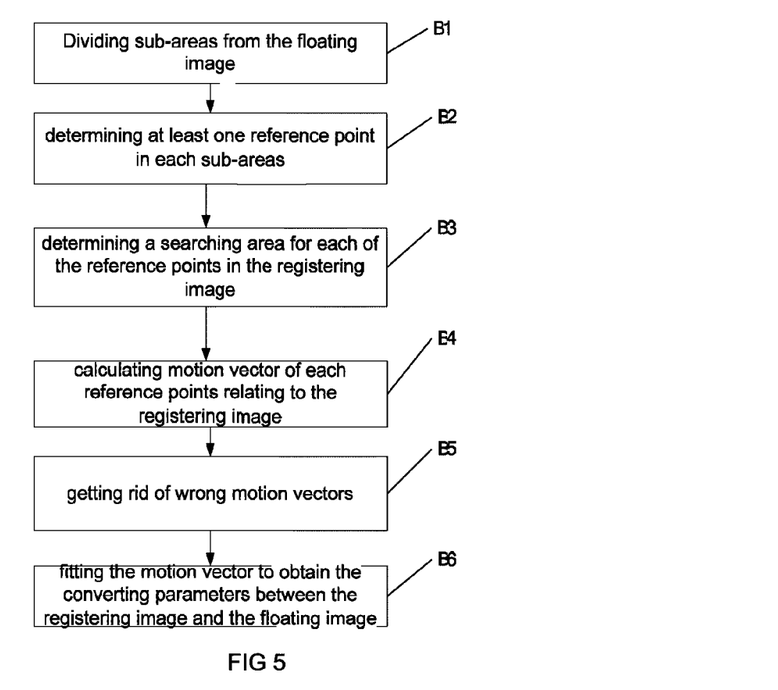
FIG. 5 is a flow diagram of an embodiment of method for registering images.

The workflow of step B is described in greater detail in FIG. 5:

Step B1: Dividing sub-areas from the floating image.

The size and shape of the sub-area are not limited. They may be set flexibly according to the actual conditions. The shape and size of the sub-areas may be the same or different. The sub-areas may be adjacent or discrete with each other. For example, in one embodiment, the floating image may be divided into sub-areas with a size of 30×30, or other size.

Step B2: determining one or more reference points in each sub-area.

The reference point(s) may be determined based on the statistical value of the gray of pixels in the sub-area, such as gradient of gray, variance of gray in a neighborhood of a point. For example, a point whose gradient of gray is the maximum among points of a sub-area may be the reference point of this sub-area. For each point in a sub-area, variance of gray in a neighborhood of this point may be calculated. Then, the point whose variance of gray is the maximum among points of the sub-area may be the reference point of the sub-area. The neighborhood of the point may include, for example, the point and 8 other points, 16 points or other number of points around the point, etc. The size of the neighborhood may also be set flexibly according to actual conditions. Similarly, other statistical values of the gray of pixels may also be used to determine the reference points.

Step B3: determining a searching area of the reference points in the registering image.

A searching area is an area designated for a reference point of the floating image in the registering image. The searching area is used to search for the matching points that are matched with the reference point. Usually, when the size of the searching area is bigger, the speed of searching out the matching point is lower, but the possibility of mistake is also lower. But for various methods of searching matching points (which will be described in detail below), the speed of searching for the matching point is not sensitive with the size of the searching area. Accordingly, it is possible to designate a searching area with big size. For example, the size of the searching area may be set as being equal to the size of the sub-area.

Step B4: calculating a motion vector of each reference point relating to the registering image using the reference point and its matching point.

Step B5: eliminating wrong motion vectors.

Because the noise of ultrasound images usually comes from the motion of tissue, not all motion vectors of the reference points are accurate. Consequently, it may be necessary to "filter" the incorrect motion vectors.

Filtering is a process of eliminating motion vectors that are offset from the set of motion vectors. There are many methods for filtering, such as, for example, clustering (clustering data and removing the points that are far away from the center, e.g., removing 10% of the points that are farthest from the center). Some test indexes may be used for judging to remove of the wrong motion vectors.

Step B6: fitting the motion vector to obtain the converting parameters between the registering image and the floating image.

There are many methods for fitting. They include, but not limited to, a LSM (Least Squares Method), a maximum likelihood method, and a Bayesian method etc.

In step B4, for each reference point of the floating image, a point that is most similar with the reference point is searched out in the searching area of the reference point. The point that has highest similarity with (hereinafter referred to as "matching with") the reference point is referred to as a "matching point". Because information carried by single point is limited, and it is difficult to match a single point with a single point, a template that is in the neighborhood around the reference point with size w×h is used to searching the matching point. The size of the template may be moderate. If the template is too small, the information carried by the template will be not enough to find out the matching point. If it is too large, not only the calculation will be increased, but also the points that are far away from the center may be misplaced when rotate angle between the floating image and the registering image is large, which will cause mistakes during searching for the matching point.

After determining the neighborhood of the reference point, a neighborhood for each point of the searching area in the registering image is determined, which is centered on the point of the searching area and has the same size with the template. Then, the similarity of the template with the neighborhood of the point of the searching area is measured by target function value. There are many methods for measuring similarity. For example, a SAD (Sum of Absolute Difference) method, a LSM method, a cross-correlation method, a mutual information method, and other methods for measuring distance of vectors may also be used. In one embodiment, the target function values obtained by these methods are collectively referred to as target function value F. For example, for the SAD method, the target function value F is smaller, the template and the neighborhood of the points of the searching area are more similar. The SAD method is described in detail below.

During extended imaging, assume that the probe is moved in a same plane. The relationship between adjacent images may be that there are translations in the depth direction, and in the direction in which the probe moves, and there are rotary movements in the scan plane. The geometric transformation of images may approximately be thought to be rigid transformation. The formula for a rigid transformation is:

$$\begin{bmatrix} \bar{x} \\ \bar{y} \end{bmatrix} = \begin{bmatrix} \cos\theta & \sin\theta \\ -\sin\theta & \cos\theta \end{bmatrix} \begin{bmatrix} x \\ y \end{bmatrix} + \begin{bmatrix} offx \\ offy \end{bmatrix}$$

We may describe the relationship of the images using relative offsets (offx, offy) and a relative rotation angle $\theta$. For convenience, offx, offy, $\theta$ are referred to as "converting parameters." When the converting parameters are determined, the relationship of the images is determined. The step for registering the floating image and the registering image is used to find out the converting parameters of the floating image and the registering image.

The SAD method is a method for measuring the similarity of templates. It measures the similarity of templates by calculating the sum of the absolute values of gray difference of corresponding points of the templates. The SAD method may be used to calculate the offset value between two images as follows:

divide one image into sub-areas;
take a template in each sub-area;
determine a searching area in the other image;
take a neighborhood having the same size with the template for each point in the searching area; and
calculate the SAD value for each neighborhood using the template and the neighborhood.

Then, the neighborhood having a minimum SAD (MSAD) value is the neighborhood that matches the template most (hereinafter "matching neighborhood"). The offset values of the center of the matching neighborhood relative to the center of the template may be the offset values that we expect between the two images.

The SAD method may also be used to calculate the rotation angle. It is similar with the process described above for calculating the offset value. The steps may include:

rotate one image in a angle scope with a predetermined angle interval; and
for each rotation location, calculate the MSAD value using the SAD method.

The rotation angle of the rotation location that has a minimum MSAD is the rotation angle we expect and the offset values calculated in this rotation location are the offset values we expect. The search is performed in three dimensions, so the number of operations in calculating the offset values and rotation angle using only the SAD method is huge.

If some points in one image and their matching point in the other image are known, the converting parameters may be obtained by fitting these points. A combined method of the SAD method and the LSM method may also be used to calculate the offset value and the rotation angle. First, the sub-areas may be divided from one image. Then, motion vectors of reference points of the sub-areas may be calculated using the SAD method. Finally, the converting parameters may be obtained by fitting the motion vectors using the LSM method.

Figure 6:
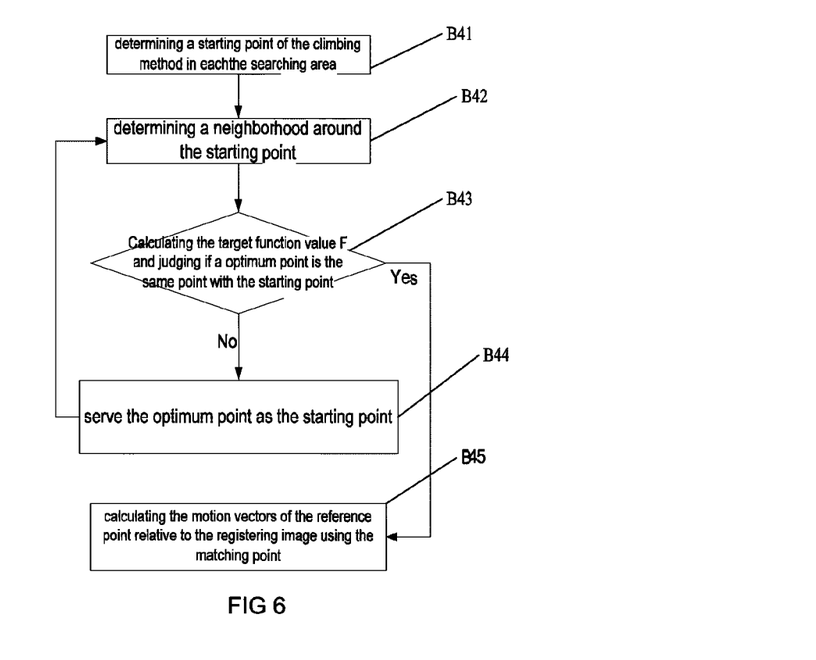
FIG. 6 is a flow diagram of an embodiment of a climbing method.

In a searching area, the optimum target function value F should be determined. One method is to search each point of the searching area one by one. That is, the target function value F for each point of the searching area may be calculated. Then, the optimum target function value F among these target function values F may be determined. In this case, the number of calculations is huge. For example, assuming that there are n reference points in a floating image, the size of each searching area is W×H, the size of template is w×h, and the method used is the SAD method, the calculation will be n×W×H×w×h. As a example, if n=100, W=40, H=20, w=20 and h=20, then the calculation is 3.2×107. Accordingly, the present disclosure includes a new method, which is referred to as "climbing method." When searching in each searching point, the climbing method judges which is the most advantageous way to determine the path to the next searching point. As shown in FIG. 6, the climbing method includes:

Step B41: determining a starting point of the climbing method in the searching area. In one embodiment, the method determines a starting point in the searching area using a "neighborhood initializing method" or a "history initializing method" (these two methods will be described below).

Step B42: determining a neighborhood around the starting point.

The size and shape of the neighborhood may be set flexibly according to real conditions. For example, it may be 3×3, 4×4, 5×5, or an irregular shape. In this embodiment, the neighborhood is set as a 3×3 area that centers on the starting point.

Step B43: Calculating the target function value F of each point in the neighborhood of the starting point of the searching area and judging if a optimum point is the same point with the starting point. If it is, step B45 is performed; otherwise step B44 is formed.

In this disclosure, the point whose target function value F is the optimum value among the target function values F of the points in the neighborhood is referred to as the "optimum point." If the optimum point is the same as the starting point, it means that the starting point is the optimum. That is, the starting point is the matching point. Accordingly, the method stops searching and performs step B45. If the optimum point isn't the same as starting point, step B44 is performed.

Step B44: designate the optimum point as the starting point and perform step B42.

Step B45: calculating the motion vectors of the reference point relative to the registering image using the matching point (the starting point).

After obtaining the matching point corresponding to the reference point of the sub-area, the motion vectors of the reference point relative to the registering image may be calculated. The motion vectors may be the offset values of the reference point relative to the matching point. The motion vector is calculated for each sub-area. Calculating the motion vectors are simple for each point in the sub-area having its individual coordinates.

The climbing method searches the matching point along a threadlike path. As a result, it is more efficient than searching each point of the searching area. Usually, it is expected that the matching point found is the optimum point among the whole searching area (hereinafter "global optimum point"), and the matching point found by the climbing method may be the optimum point among a local area (hereinafter "local optimum point"). In the searching area, there may be two or more local optimum points. The global optimum point is the most optimum one among the local optimum points.

Figure 7:
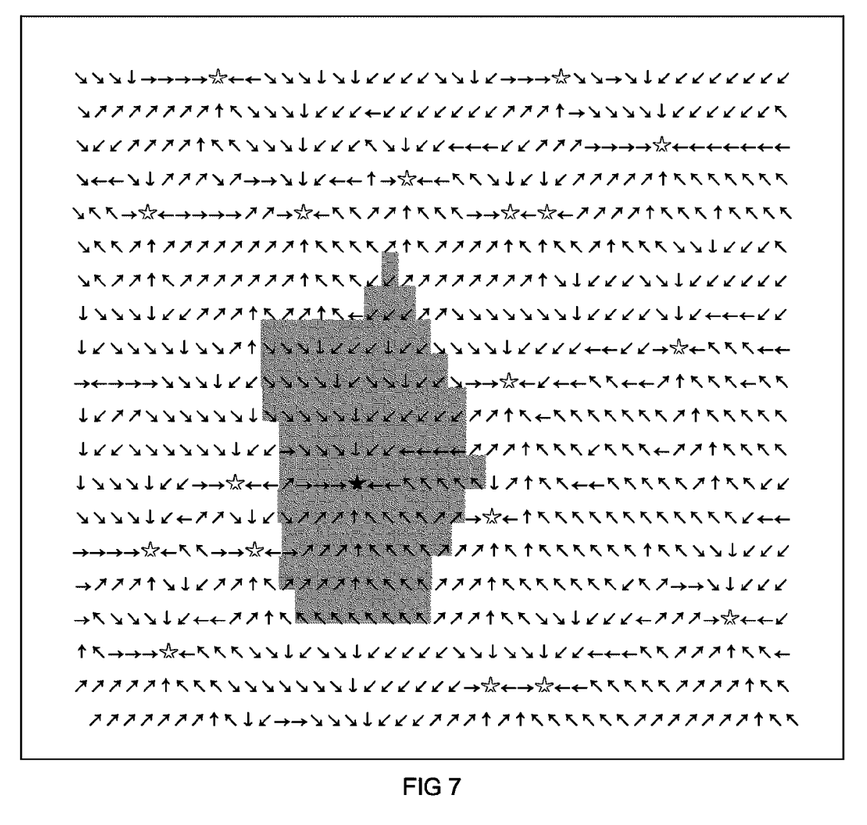
FIG. 7 is a schematic diagram of an embodiment of a climbing method.

FIG. 7 shows an example of the climbing method. As shown in FIG. 7, the solid star is the global optimum point. The hollow stars are other local optimum points. The arrows show the directions from points that are not optimum points to their optimum points. From FIG. 7, we can see that whichever point from which the climbing method start, it will always get to one of the local optimum points. The climbing method starting from different points may get to the same local optimum point, or get to different local optimum points respectively. It depends on location of the starting point of the climbing method. In this disclosure, the group of points from which the climbing methods start and get to a same local optimum point is referred to as "radiation area" of the local optimum point. For example, the area with gray background is the radiation area of the global optimum point. In actual conditions, the difference between the target function values F of adjacent points is usually small, so usually the radiation area of the global optimum point is the largest one, or, at least a larger one.

In order to make the climbing method get to the global optimum point, controlling the location of the starting point may be used. That is, if the starting point of the climbing method is located in the radiation area of the global optimum point, not in that of other local optimum point, the climbing method will certainly get to the global optimum point.

In fact, controlling the location of the starting point is essentially forecasting to the global optimum point. If the starting point forecasted is near to the global optimum point, the success ratio of the climbing method may be increased.

The location of the starting point may be forecasted using existing information. There are many methods for forecasting the location. In one embodiment, a method for forecasting the location of the starting point based on information of neighborhood (hereinafter "neighborhood initializing method") is disclosed. In another embodiment, a method for forecasting the location of the starting point based on history information (hereinafter "history initializing method") is disclosed. However, the methods for forecasting the location of the starting point are not limited on these two methods. Other similar methods may also be used.

1. Neighborhood Initializing Method

Usually, in the same frame, because the adjacent sub-area is close in space, the motion vectors of reference points in adjacent sub-areas are similar, on which the neighborhood initializing method is based. By the neighborhood initializing method, the starting point is obtained using the motion vector of the reference point of the adjacent sub-area that was calculated already. For example, in the current sub-area, the method may draw a vector that is equal to the motion vector of reference point of the adjacent sub-area starting from the reference point of the current sub-area and ending at an end point. This vector has a starting point (the reference point of the current sub-area) and an end point. Then, the method may find the point that has the same location as the end point in the searching area. This point having the same location as the end point is designated as the starting point of the climbing method. Then, the method may search the matching point matching with the reference point of current sub-area using the climbing method starting from the starting point and calculate the motion vector of the reference point of the current sub-area. The calculated motion vector of the reference point of the current sub-area then is used to obtain the starting point for next sub-area that is adjacent to the current sub-area and was not searched by the similar way above. Then, the matching point of the next sub-area may be found out using the climbing method starting from the starting point and the motion vector may be calculated. The process is repeated until all of the sub-areas are searched. In this way, it may be ensured that the starting points always locate within the bigger radiation area of the sub-area and the optimum point searched out is the global optimum point.

Figure 8:
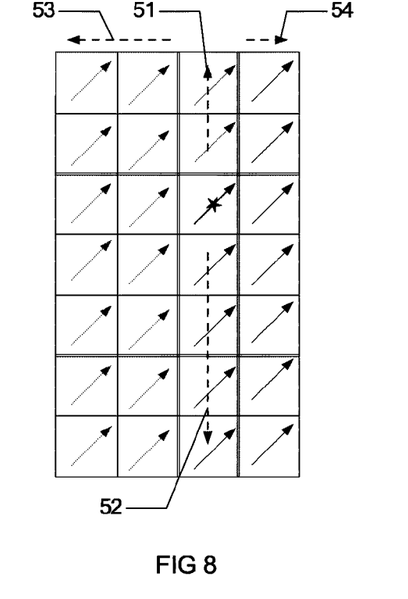
FIG. 8 is a schematic diagram of an embodiment of a neighborhood initializing method.
Figure 9:
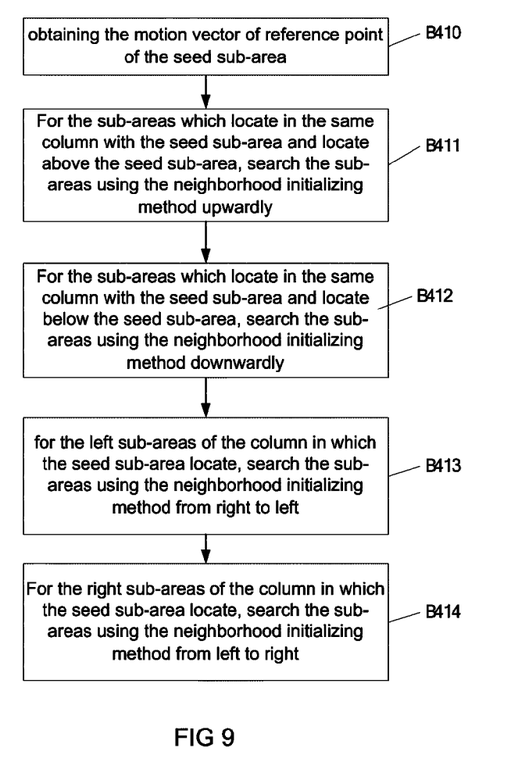
FIG. 9 is a flow diagram of an embodiment of a neighborhood initializing method.

The idea of the neighborhood initializing method is to obtain an end point starting from the reference point of the current sub-area according to the motion vector of an adjacent sub-area that was calculated already and designate the point in the searching area that has the same location as the end point as the starting point of the climbing method. An embodiment of the neighborhood initializing method is shown in FIG. 8. In FIG. 8, the sub-area marked with ★ is a "seed sub-area," the solid arrows represent the motion vectors of the reference points of the sub-areas, and the dotted line arrows represent the sequence in which the sub-areas are searched using the neighborhood initializing method. The method of this embodiment includes:

Step B410: obtaining the motion vector of reference point of the seed sub-area.

When using the neighborhood initializing method, there may be at least one sub-area whose reference point's motion vector is the base of obtaining the starting points of other sub-areas and is not obtained using the climbing method. This kind of sub-area is referred to as "seed sub-area" in this disclosure. The seed sub-area may be located at any location of the floating image. But the accuracy of the motion vector calculated from the seed sub-area will directly influence the accuracy of the motion vectors calculated for other sub-areas. So, the seed sub-area may be sub-area with distinct features. The seed sub-area may be selected according to some rules, such as the seed sub-area may be selected based on the statistical parameters of gray. For example, the sub-area with maximum gradient, with maximum variance, or with maximum mean may be selected as the seed sub-area.

For the seed sub-area, it may be needed to search the matching point using other searching methods and then calculate the motion vector. For example, the method may search the whole area (hereinafter "global searching method") of the seed sub-area to find the matching point. Although the global searching method is slow, it is used for only seed sub-area. As a result, the speed of the whole neighborhood initializing method will not be significantly influenced.

After obtaining the motion vector of the reference point of the seed sub-area, for the sub-area that is adjacent to the seed sub-area, the method may obtain an end point starting from the reference point of the sub-area according to the motion vector of the reference point of the seed sub-area. Then, the method may designate the point in the searching area that has the same location as the end point as the starting point of the climbing method, search out the matching point using the climbing method, and then calculate the motion vector of the reference point of the sub-area. Thereafter, the method may use the motion vector of the reference point of the sub-area to obtain the starting point of other sub-areas to search out the matching point and calculate the motion vector of those sub-areas. The method may repeat until the motion vectors of reference point of all sub-areas are calculated.

Step B411: For the sub-areas that are located in the same column with the seed sub-area and are located above the seed sub-area, the method may search the sub-areas using the neighborhood initializing method upwardly (shown by the dotted line arrow marked as 51 in FIG. 8).

Step B412: For the sub-areas that are located in the same column with the seed sub-area and located below the seed sub-area, the method may search the sub-areas using the neighborhood initializing method downwardly (shown by the dotted line arrow marked as 52 in FIG. 8).

Step B413: After the step B411 and the step B412, the motion vectors of the reference points of all of the sub-areas located in the same column with the seed sub-area are obtained. Then, for the left sub-areas of the column in which the seed sub-area is located, the method may search the sub-areas using the neighborhood initializing method from right to left (shown by the dotted line arrow marked as 53 in FIG. 8).

Step B414: For the right sub-areas of the column in which the seed sub-area are located, the method may search the sub-areas using the neighborhood initializing method from left to right (shown by the dotted line arrow marked as 54 in FIG. 8).

The sequences in which the sub-areas are searched using the neighborhood initializing method are not limited by the sequences described in above embodiment. Other sequences may also be used to search the sub-areas.

Based on the method for obtaining the starting point described above, in one embodiment, the determining sub-unit 2441 includes a seed sub-area determining sub-unit, a calculating sub-unit, and the first starting point obtaining sub-unit. The seed sub-area determining sub-unit is configured to determine the seed sub-area. The calculating sub-unit is configured to calculate the motion vector of the reference point of the seed sub-area relative to the floating image. The first starting point obtaining sub-unit is configured to obtain the starting point of the sub-areas.

For the sub-areas that are adjacent to the seed sub-area, the first starting point obtaining sub-unit obtains an end point starting from the reference point of the sub-area according to the motion vector of the reference point of the seed sub-area, then the point in the searching area that has the same location as the end point is designated as the starting point. For the sub-areas that are not adjacent to the seed sub-area, the first starting point obtaining sub-unit obtains an end point starting from the reference point of the sub-area according to the motion vector of the reference point of the sub-area that is adjacent to the sub-area, then the point in the searching area that has the same location as the end point is designated as the starting point.

2. History Initializing Method.

Usually the frame rate of an ultrasound imaging system is relatively high, and the users usually scan at an even speed. Thus, the motion vectors of the areas that have the same location in adjacent frames are similar. In one embodiment, the starting points of sub-areas of current image may be obtained based on the motion vectors of the reference points of the sub-areas that have the same location in the "history" image that is adjacent to the current image. Then, the matching point of the sub-areas may be searched using the climbing method starting from the starting point.

The history initializing method obtains an end point starting from the reference point of the current sub-area according to the "history" motion vector at the same location as current sub-area, then the point in the searching area that has the same location as the end point is designated as the starting point.

Figure 10:
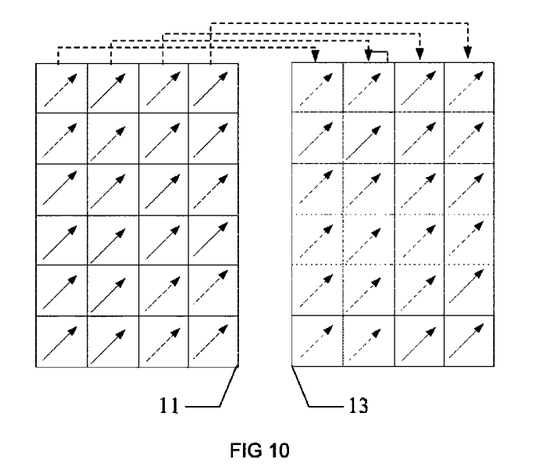
FIG. 10 is a schematic diagram of an embodiment of a history initializing method.
Figure 11:
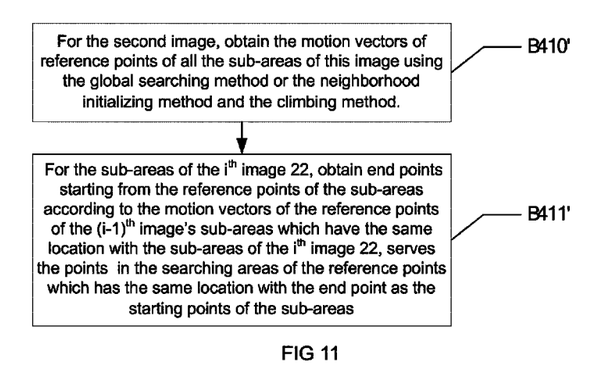
FIG. 11 is a flow diagram of an embodiment of history initializing method.

An embodiment using the history initializing method is shown in FIG. 10. In FIG. 10, the solid line arrows represent the motion vectors. The dotted line arrows illustrate that the starting points of the sub-areas of current image 13 (the ith image, i>2) are obtained using the motion vectors of the reference points of the sub-areas of previous image 11 (the (i−1)th frame). The method of this embodiment includes:

Step B410': For the second image (the first image was initialized as registering image; the second image is the image to be registered first time), obtain the motion vectors of reference points of all the sub-areas of this image using the global searching method or the neighborhood initializing method and the climbing method.

Step B411': For the sub-areas of the ith image 13, the method may obtain end points starting from the reference points of the sub-areas according to the motion vectors of the reference points of the (i−1)th image's sub-areas that have the same location as the sub-areas of the ith image 13, then designate the points in the searching areas of the reference points of the sub-area that has the same location as the end point as the starting points of the sub-areas.

In other embodiments, the motion vectors of the image that have an interval of one or more images with the current image may be used to obtain the starting point of sub-areas of current image. For example, the motion vectors of the (i−2)th image, the (i−3)th image, or image having more interval images with current image may be used to obtain the starting point of the current image. Alternatively, the motion vectors of all the several previous images may be use at the same time to obtain the starting point of the current image. All the method for obtaining the starting point of current image using the motion vectors of one or more previous images are considered to be within the scope of this disclosure.

The neighborhood initializing method and the history initializing method may be used separately or together. For example, the method may calculate the weighted average of the motion vector of the reference point of adjacent sub-area and the motion vector of the reference point of the previous image's sub-area that has the same location as the current sub-area, then obtain an end point starting from the reference point of the current sub-area according to the weighted average, then designate the point in the searching area of the reference point that has the same location as the end point as the starting point of the climbing method and use the climbing method starting from the starting point to find out the matching point of the current sub-area.

Based on the history initializing method for obtaining the starting point described above, in one embodiment, the determining sub-unit 2441 includes history motion vector obtaining sub-unit and the second starting point obtaining sub-unit. The history motion vector obtaining sub-unit is configured to obtain the motion vectors of reference points of the sub-areas of previous floating image(s) (hereinafter "history floating image"). The second starting point obtaining sub-unit is configured to obtain an end point starting from the reference point of the current sub-area according to the motion vector of the previous frame's sub-area that has the same location as current sub-area, then designate the point in the searching area of the reference point of the current sub-area that has the same location as the end point as the starting point.

After registering the floating image and the registering image, the method may judge whether the floating image may be spliced. By this way, the stability and the fault-tolerance capability of the method may be improved. The rules for the judgment may be set according to real conditions. For example, the motion vectors of the sub-areas may be not irregular because of the quality of the images. Thus, when fitting the motion vectors, a large angle may be obtained. When making the judgment, the rules may be set as: if the angle obtained from the fitting process is greater than a threshold, the floating image will not be spliced. The threshold may be set flexibly according to real conditions. For example, it may be between 2-6 degrees, such as 4 degrees.

The judgment step is not necessary. The floating image may be directly spliced after the registering step without the judgment step.

If the result of the judgment step is that the floating image may be spliced, then the floating image will be spliced to the registering image.

Step D: Splicing the floating image and the registering image according to the converting parameters.

In the description above, numerous specific details are provided for a thorough understanding of the embodiments described herein. However, those of skill in the art will recognize that one or more of the specific details may be omitted, or other methods, components, or materials may be used. In some cases, operations are not shown or described in detail.

Furthermore, the described features, operations, or characteristics may be combined in any suitable manner in one or more embodiments. It will also be readily understood that the order of the steps or actions of the methods described in connection with the embodiments disclosed may be changed as would be apparent to those skilled in the art. Thus, any order in the drawings or Detailed Description is for illustrative purposes only and is not meant to imply a required order, unless specified to require an order.

Embodiments may include various steps, which may be embodied in machine-executable instructions to be executed by a general-purpose or special-purpose computer (or other electronic device). Alternatively, the steps may be performed by hardware components that include specific logic for performing the steps or by a combination of hardware, software, and/or firmware.

Embodiments may also be provided as a computer program product including a machine-readable medium having stored thereon instructions that may be used to program a computer (or other electronic device) to perform processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/machine-readable medium suitable for storing electronic instructions.

Those of skill in the art would further appreciate that the various illustrative logical blocks, modules, circuits, and algorithm steps described in connection with the embodiments disclosed herein may be implemented as electronic hardware, computer software, or combinations of both. To illustrate the interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the invention as claimed hereinafter.

the invention claimed is:

1. A method for registering images, comprising:
   determining a floating image and a registering image;
   dividing sub-areas from the floating image;
   determining one or more reference points in each sub-area;
   determining searching areas in the registering image for the one or more reference points;
   searching for matching points matching with the reference points in the searching areas corresponding to the reference points;
   calculating motion vectors of the reference points relative to the registering image according to the matching points; and
   fitting the motion vectors to obtain converting parameters between the floating image and the registering image.

2. The method of claim 1, wherein searching comprises:
   determining a starting point in the searching area;
   determining a neighborhood around the starting point;
   calculating target function value of the points in the neighborhood;
   finding an optimum point among the points in the neighborhood whose target function value is an optimum value;
   designating the starting point as the matching point in response to the starting point being the optimum point; and
   designating the optimum point as the starting point and repeating the determining neighborhood step, the calculating the target function value step, the finding optimum point step, and the designating the starting point step in response to the starting point not being the optimum point.

3. The method of claim 2, wherein determining a starting point in the searching area comprises:
   determining a seed sub-area;
   obtaining motion vectors of reference points of the seed sub-area relative to the registering image; and
   for the sub-area that is adjacent to the seed sub-area, obtaining an end point starting from the reference point of the sub-area according to the motion vector of the reference point of the seed sub-area and designating a point in the searching area corresponding to the reference point of the sub-area that has the same location as the end point as the starting point.

4. The method of claim 3, further comprising:
   for the sub-area that is not adjacent to the seed sub-area, obtaining an end point starting from the reference point of the sub-area according to the motion vector of the reference point of an adjacent sub-area that was obtained already and designating a point in the searching area corresponding to the reference point of the sub-area that has the same location as the end point as the starting point.

5. The method of claim 3, wherein determining the seed sub-area comprises: selecting the sub-area that has a maximum statistical value of gray as the seed sub-area.

6. The method of claim 3, wherein obtaining motion vectors of reference points of the seed sub-area relative to the registering image comprises:
   using a global searching method to obtain the motion vectors of reference points of the seed sub-area relative to the registering image.

7. The method of claim 2, wherein determining a starting point in the searching area comprises:
   obtaining motion vectors of reference points of sub-areas of a history floating image; and
   obtaining an end point starting from the reference point of the sub-area according to the motion vector of reference points of sub-areas of the history floating image that has the same location as the sub-area and designating the point in the searching area corresponding to the reference point of the sub-area that has the same location as the end point as the starting point.

8. The method of claim 7, wherein obtaining motion vectors of reference points of sub-areas of history floating image comprises:
   using a global searching method to calculate the motion vectors of the reference points of the sub-area of the history floating image.

9. The method of claim 2, wherein determining a starting point in the searching area comprises:
  calculating the weighted average of the motion vector of the reference point of an adjacent sub-area and the motion vector of the reference point of the sub-area that has the same location as the sub-area of a history floating image; and
  obtaining an end point starting from the reference point of the sub-area according to the weighted average and designating the point in the searching area corresponding to the reference point of the sub-area that has the same location as the end point as the starting point.

10. The method of claim 1, wherein determining one or more reference points in each sub-area comprises:
  selecting a point in the sub-area that has a maximum statistical value of gray as the reference point.

11. The method of claim 1, wherein determining a floating image and a registering image comprises:
  receiving an image to be registered;
  designating the image as the registering image in response to the image being the first image received to be registered; and
  designating the image as the floating image in response to the image being not the first image received to be registered.

12. The method of claim 1, further comprising:
  removing wrong motion vectors before fitting the motion vectors.

13. A method for extended imaging, comprising:
  determining a floating image and a registering image;
  dividing sub-areas from the floating image;
  determining one or more reference points in each sub-area;
  determining searching areas in the registering image for each reference point;
  searching matching points matching with the reference points in the searching areas corresponding to the reference points;
  calculating motion vectors of the reference points relative to the registering image according to the matching points;
  fitting the motion vectors to obtain converting parameters between the floating image and the registering image; and
  splicing the floating image and the registering image according to the converting parameters.

14. The method of claim 13, wherein, before splicing the floating image and the registering image, the method further comprises:
  stopping splicing the floating image and the registering image in response to one or more predetermined conditions being satisfied.

15. The method of claim 13, wherein at least one predetermined condition is an angle obtained by fitting the motion vectors is larger than a threshold.

16. A method for ultrasound imaging, comprising:
  transmitting ultrasound waves;
  receiving ultrasound echoes;
  processing the ultrasound echoes to obtain ultrasound images;
  determining a floating image and a registering image;
  dividing sub-areas from the floating image;
  determining one or more reference points in each sub-area;
  determining searching areas in the registering image for the reference points;
  searching matching points matching with the reference points in the searching areas corresponding to the reference points;
  calculating motion vectors of the reference points relative to the registering image according to the matching points;
  fitting the motion vectors to obtain converting parameters between the floating image and the registering image;
  splicing the floating image and the registering image according to the converting parameters; and
  displaying the spliced image.

17. An apparatus for registering images, comprising:
  a floating image and registering image determining unit configured to determine a floating image and a registering image;
  a sub-area dividing sub-unit configured to divide sub-areas from the floating image;
  a reference point determining sub-unit configured to determine one or more reference points in each sub-area;
  a searching area determining sub-unit configured to determine searching areas in the registering image for the reference points;
  a motion vector processing sub-unit configured to search matching points matching with the reference points in the searching areas corresponding to the reference points and calculate motion vectors of the reference points relative to the registering image according to the matching points; and
  a motion vector fitting sub-unit configured to fit the motion vectors to obtain converting parameters between the floating image and the registering image.

18. The apparatus of claim 17, wherein the motion vector processing sub-unit comprises:
  a determining sub-unit configured to determine starting point in the searching area; and
  a motion vector calculating sub-unit configured to determine a neighborhood around the starting point, calculate the target function value of the points in the neighborhood, find an optimum point among the points in the neighborhood whose target function value is the optimum value, designate the starting point as the matching point in response to the starting point being the optimum point, and designate the optimum point as starting point and repeating the determining neighborhood step, the calculating the target function value step, the finding optimum point step, and the designating the starting point step in response to the starting point being not the optimum point.

19. The apparatus of claim 18, wherein the determining sub-unit comprises:
  a seed sub-area determining sub-unit configured to determine the seed sub-area;
  a calculating sub-unit configured to calculate the motion vector of the reference point of the seed sub-area relative to the floating image;
  a first starting point obtaining sub-unit configured to obtain the starting point, wherein
  for the sub-area that is adjacent to the seed sub-area, an end point starting from the reference point of the sub-area is obtained according to the motion vector of the reference point of the seed sub-area, and a point in the searching area corresponding to the reference point of the sub-area that has the same location is designated as the end point as the starting point; and
  for the sub-area that is not adjacent to the seed sub-area, an end point starting from the reference point of the sub-area is obtained according to the motion vector of the reference point of adjacent sub-area that was obtained already, and a point in the searching area corresponding to the reference point of the sub-area is designated that has the same location as the end point as the starting point.

20. The apparatus of claim 18, wherein the determining sub-unit comprises:
   an history motion vector obtaining sub-unit configured to obtain the motion vectors of reference points of the sub-areas of a history floating image; and
   a second starting point obtaining sub-unit configured to obtain an end point starting from the reference point of the sub-area according to the motion vector of reference points of sub-areas of history floating image that has the same location as the sub-area and designate the point in the searching area corresponding to the reference point of the sub-area that has the same location as the end point as the starting point.

21. The apparatus of claim 17, further comprising a motion vector filtering sub-unit configured to eliminate wrong motion vectors, the motion vector filtering sub-unit located between the motion vector processing sub-unit and the motion vector fitting sub-unit.

22. The apparatus of claim 17, wherein the floating image and registering image determining unit comprises:
   a images receiving sub-unit configured to receive images;
   a judging for registering image initializing sub-unit configured to judge whether the registering image need to be initialized; and
   a registering image initializing sub-unit configured to initialize an image as the registering image.

23. A system for extended imaging, comprising:
   a floating/registering image determining unit configured to determine a floating image and a registering image;
   a sub-area dividing sub-unit configured to divide sub-areas from the floating image;
   a reference point determining sub-unit configured to determine one or more reference points in each sub-area;
   a searching area determining sub-unit configured to determine searching areas in the registering image for the reference points;
   a motion vector processing sub-unit configured to search matching points matching with the reference points in the searching areas corresponding to the reference points and calculate motion vectors of the reference points relative to the registering image according to the matching points;
   a motion vector fitting sub-unit configured to fit the motion vectors to obtain converting parameters between the floating image and the registering image;
   a splicing unit configured to splice the floating image and the registering image according to the converting parameters; and
   an outputting unit configured to output the spliced extended image for displaying.

24. A system for ultrasound imaging including a probe, a beam former, a signal processor, a DSC module, an extended imaging sub-system, and a display, wherein the extended imaging sub-system comprises:
   a floating/registering image determining unit configured to determine a floating image and a registering image;
   a sub-area dividing sub-unit configured to divide sub-areas from the floating image;
   a reference point determining sub-unit configured to determine one or more reference points in each sub-area;
   a searching area determining sub-unit configured to determine searching areas in the registering image for the reference points;
   a motion vector processing sub-unit configured to search matching points matching with the reference points in the searching areas corresponding to the reference points and calculate motion vectors of the reference points relative to the registering image according to the matching points;
   a motion vector fitting sub-unit configured to fit the motion vectors to obtain converting parameters between the floating image and the registering image;
   a splicing unit configured to splice the floating image and the registering image according to the converting parameters; and
   an outputting unit configured to output the spliced extended image for display.

* * * * *